(12) United States Patent
Chen et al.

(10) Patent No.: US 10,256,002 B2
(45) Date of Patent: Apr. 9, 2019

(54) SUPPORT STRUCTURE AND HIGHLY ALIGNED MONOCHROMATIC X-RAY OPTICS FOR X-RAY ANALYSIS ENGINES AND ANALYZERS

(71) Applicant: X-RAY OPTICAL SYSTEMS, INC., East Greenbush, NY (US)

(72) Inventors: Zewu Chen, Schenectady, NY (US); Rory D. Delaney, Slingerlands, NY (US); John H. Burdett, Charlton, NY (US); Kai Xin, Wynantskill, NY (US)

(73) Assignee: X-RAY OPTICAL SYSTEMS, INC., East Greenbush, NY (US)

(*) Notice: Subject to any disclaimer, the term of this patent is extended or adjusted under 35 U.S.C. 154(b) by 0 days.

(21) Appl. No.: 15/334,886

(22) Filed: Oct. 26, 2016

(65) Prior Publication Data
US 2017/0110212 A1 Apr. 20, 2017

Related U.S. Application Data

(62) Division of application No. 14/128,078, filed as application No. PCT/US2012/061900 on Oct. 25, 2012, now abandoned.
(Continued)

(51) Int. Cl.
*G21K 1/06* (2006.01)
*G01N 23/207* (2018.01)
*G01N 23/223* (2006.01)

(52) U.S. Cl.
CPC ............ *G21K 1/06* (2013.01); *G01N 23/223* (2013.01); *G01N 23/2076* (2013.01);
(Continued)

(58) Field of Classification Search
CPC ....... G01N 2223/076; G01N 2223/315; G01N 23/2076; G01N 23/223; G21K 1/06; G21K 2201/064
See application file for complete search history.

(56) References Cited

U.S. PATENT DOCUMENTS

| 3,777,156 A | 12/1973 | Hammond et al. |
| 5,004,319 A * | 4/1991 | Smither ............... G02B 3/00 359/291 |

(Continued)

FOREIGN PATENT DOCUMENTS

| CN | 101356589 A | 1/2009 |
| CN | 101981651 A | 2/2011 |

(Continued)

OTHER PUBLICATIONS

Sellick, Barton O., "Formation and Evaluation of Convex-Curved Crystals of Lithium Fluoride for Use in Analyzing X-Ray Spectra—UCRL-52086", The International Nuclear Information System (INIS), XP055362981, Jul. 22, 1976 (21 pages).
(Continued)

*Primary Examiner* — Chih-Cheng Kao
(74) *Attorney, Agent, or Firm* — Kevin P. Radigan, Esq.; Heslin Rothenberg Farley & Mesiti P.C.

(57) ABSTRACT

A support structure having multiple highly aligned curved x-ray optics, the support structure having multiple internal partially or fully concentric surfaces upon which said optics are mounted, thereby aligning said optics along a central optical axis thereof and therefore to a source, sample, and/or detector in combination with which the support structure is useable. The surfaces may be nested around the central optical axis; and the support structure may divided longitudinally into sections around the central optical axis by walls. At least one of the x-ray optics comprises a curved diffracting optic, for receiving a diverging x-ray beam and focusing
(Continued)

the beam to a focal area, in one embodiment a focusing monochromating optic. In an improved embodiment, an optic comprises a single layer, plastically deformed, LiF optic.

7 Claims, 15 Drawing Sheets

Related U.S. Application Data

(60) Provisional application No. 61/551,602, filed on Oct. 26, 2011.

(52) U.S. Cl.
CPC . *G01N 2223/076* (2013.01); *G01N 2223/308* (2013.01); *G01N 2223/315* (2013.01); *G21K 2201/064* (2013.01)

(56) References Cited

U.S. PATENT DOCUMENTS

| | | | |
|---|---|---|---|
| 5,175,755 | A | 12/1992 | Kumakhov |
| 5,192,869 | A | 3/1993 | Kumakhov |
| 5,497,008 | A | 3/1996 | Kumakhov |
| 5,570,408 | A | 10/1996 | Gibson |
| 5,604,353 | A | 2/1997 | Gibson et al. |
| 5,745,547 | A | 4/1998 | Xiao |
| 5,761,526 | A | 6/1998 | Inoue et al. |
| 6,249,566 | B1* | 6/2001 | Hayashi ............ G21K 1/06 378/84 |
| 6,285,506 | B1 | 9/2001 | Chen |
| 6,317,483 | B1 | 11/2001 | Chen |
| 7,035,374 | B2 | 4/2006 | Chen |
| 7,072,439 | B2 | 7/2006 | Radley et al. |
| 7,110,506 | B2 | 9/2006 | Radley et al. |
| 7,209,545 | B2 | 4/2007 | Radley et al. |
| 7,583,789 | B1 | 9/2009 | Chen et al. |
| 7,738,629 | B2 | 6/2010 | Chen |
| 7,738,630 | B2 | 6/2010 | Burdett, Jr. et al. |
| 2004/0131146 | A1* | 7/2004 | Chen ............ G21K 1/06 378/41 |
| 2006/0093253 | A1 | 5/2006 | Egle et al. |
| 2007/0209393 | A1 | 9/2007 | Miller et al. |
| 2008/0044075 | A1* | 2/2008 | Gautier ............ G01N 23/2076 382/132 |
| 2009/0225947 | A1 | 9/2009 | MacDonald et al. |
| 2009/0225948 | A1 | 9/2009 | Burdett, Jr. et al. |
| 2011/0170666 | A1 | 7/2011 | Chen et al. |
| 2014/0294157 | A1 | 10/2014 | Chen et al. |

FOREIGN PATENT DOCUMENTS

| | | |
|---|---|---|
| JP | 2002195963 A | 7/2002 |
| JP | 2005534921 A | 11/2005 |
| JP | 2007-536754 A | 12/2007 |
| JP | 2011513751 A | 4/2011 |
| WO | WO 2006/022333 A1 | 3/2006 |
| WO | WO 2008/085500 A2 | 7/2008 |
| WO | WO 2009111454 A1 * | 9/2009 ........... G01N 23/223 |

OTHER PUBLICATIONS

Sellick, Barton O., "Modification of the X-Ray Diffraction Efficiency of Lithium Fluoride Crystals by Surface Treatment—UCRL-52087", The International Nuclear Information System (INIS), XP055362977, Jul. 22, 1976 (9 pages).

Extended European Search Report (EESR) for EP Application No. 16 20 0180, dated Apr. 19, 2017 (12 pages).

Chen et al., International Search Report for PCT/US2012/061900 (PCT Publication No. WO 2008/085500 A2), dated Feb. 28, 2013 (2 pages).

Chen et al., Restriction Requirement for U.S. Appl. No. 14/128,078, filed Dec. 20, 2013 (U.S. Patent Publication No. 2014/0291457 A1), dated Sep. 1, 2015.

Chen et al., Office Action for U.S. Appl. No. 14/128,078, filed Dec. 20, 2013 (U.S. Patent Publication No. 2014/0291457 A1), dated Nov. 5, 2015.

Chen et al., Final Office Action for U.S. Appl. No. 14/128,078, filed Dec. 20, 2013 (U.S. Patent Publication No. 2014/0291457 A1), dated Apr. 26, 2016.

* cited by examiner

FIG. 13B

Cl (coating | subtrate) — Pass
- 0 ppm ± 0
- 0.00 ug/cm²
- 432672 ppm ± 11113 — Fail

Se (coating | subtrate) — Fail
- 103 ppm ± 12
- 0.67 ug/cm²
- Not Detected

Cd (coating | subtrate) — Not Detected / Not Detected

Sb (coating | subtrate) — Not Detected / Not Detected

Br (coating | subtrate) — Not Detected / Not Detected

Pb (coating | subtrate) — Fail
- 133 ppm ± 26
- 0.87 ug/cm²
- Not Detected

Ba (coating | subtrate) — Not Detected / Not Detected

Ha (coating | subtrate) — Not Detected / Not Detected

As (coating | subtrate) — Pass
- 18.6 ppm ± 12
- 0.12 ug/cm²

Cr (coating | subtrate) — Not Detected / Not Detected

SUPPORT STRUCTURE AND HIGHLY ALIGNED MONOCHROMATIC X-RAY OPTICS FOR X-RAY ANALYSIS ENGINES AND ANALYZERS

RELATED APPLICATION INFORMATION

This application is a divisional of U.S. patent application Ser. No. 14/128,078, filed Dec. 20, 2013, which claims priority from PCT Application No. PCT/US2012/061900, filed Oct. 25, 2012, which claims the benefit of U.S. provisional patent application Ser. No. 61/551,602, filed Oct. 26, 2011. Each of these applications is hereby incorporated herein by reference in its entirety.

This application also relates to U.S. Pat. No. 6,934,359 B2, issued Aug. 23, 2005, entitled "XRF System Including Focusing Optic on Excitation Side and Monochromatic Collection"; U.S. Pat. No. 7,738,630 B2, issued Jun. 16, 2010, entitled "Highly Aligned X-Ray Optic and Source Assembly for Precision X-Ray Analysis Applications"; and U.S. Patent Publication No. 2011/0170666 A1, published Jul. 14, 2011, entitled "XRF System Having Multiple Excitation Energy Bands in Highly Aligned Package", each of which is assigned to X-Ray Optical Systems, Inc., the assignee of the present invention, and each of which is hereby incorporated herein by reference in its entirety.

BACKGROUND OF THE INVENTION

Current events, e.g., the discovery of toxins in toys, environmental air and water concerns, and resulting regulations dictate an urgent need for an analyzer for toxic element determination. Advanced x-ray fluorescence (XRF) analyzers can play a valuable role in the quantification of such toxins and many other substances of interest in a variety of samples, e.g., toxins in consumer products, and various harmful elements in petroleum products.

As one prominent example, manufacturers, suppliers, distributors, retailers, and regulatory entities need a long-term solution for toxic-element analysis for a wide variety of consumer goods. Many new regulations require manufacturers to detect many elements such as lead (Pb), mercury (Hg), arsenic (As), cadmium (Cd), chromium (Cr), bromine (Br), selenium (Se), antimony (Sb), barium (Ba), and chlorine (Cl). In the EU regulations, the maximum concentration in a homogenous material is 1,000 ppm for hexavalent chromium ($Cr^{6+}$), Hg, Pb, polybrominated biphenyl (PBB), and polybrominated diphenyl ethers (PBDE), and 100 ppm for Cd. The new U.S. regulation (CPSIA) for children's products is much more restrictive. For example, the maximum allowable lead level in toys and children's jewelry is less than or equal to 100 ppm in any accessible part of a product.

Current measurement methods are either accurate enough but not usable on the factory floor, or they may be convenient for use on the factory floor but not close to being sufficiently sensitive or repeatable. As a result, there is a need for a truly fit-for-purpose analyzer for this application.

More generally, there is a strong market need for a rapid, reliable, convenient, nondestructive, high-sensitivity, quantitative, cost-effective analyzer to carry out critical and conclusive measurements with a single instrument in a manufacturing facility either at-line or on-line, or any place in a distribution chain. Contaminated products can be eliminated at the most advantageous place in the process, substantially mitigating or even eliminating accidental production waste and errors. There is also a strong need for a similar capability at several stages in the distribution and by regulators to verify the compliance of materials and products.

In x-ray analysis systems, high x-ray beam intensity and small beam spot sizes are important to reduce sample exposure times, increase spatial resolution, and consequently, improve the signal-to-background ratio and overall quality of x-ray analysis measurements. In the past, expensive and powerful x-ray sources in the laboratory, such as rotating anode x-ray tubes or synchrotrons, were the only options available to produce high-intensity x-ray beams. Recently, the development of x-ray optics enables collection of the diverging radiation from an x-ray source by focusing the x-rays. A combination of x-ray focusing optics and small, low-power x-ray sources can produce x-ray beams with intensities comparable to those achieved with larger, high-power, and more expensive devices. As a result, systems based on a combination of small, inexpensive x-ray sources, excitation optics, and collection optics are greatly expanding the availability and capabilities of x-ray analysis equipment in, for example, small laboratories and in the field, factory, or clinic, etc.

Monochromatization of x-ray beams in the excitation and/or detection paths is also useful to excite and/or detect very precise portions of the x-ray energy spectrum corresponding to various elements of interest (lead, etc.). X-ray monochromatization technology is based on diffraction of x-rays on optical crystals, for example, germanium (Ge) or silicon (Si) crystals. Curved crystals can provide deflection of diverging radiation from an x-ray source onto a target, as well as providing monochromatization of photons reaching the target. Two common types of curved crystals are known as singly-curved crystals and doubly-curved crystals (DCCs). Using what is known in the art as Rowland circle geometry, singly-curved crystals provide focusing in two dimensions, leaving x-ray radiation unfocused in the third or orthogonal plane. Doubly-curved crystals provide focusing of x-rays from the source to a point target in all three dimensions. This three-dimensional focusing is referred to in the art as "point-to-point" focusing.

The present invention addresses challenges presented in the fabrication and mounting of such monochromating optics in new x-ray analysis systems, in which performance and alignment improvements are continually needed, along with decreases in size, weight, power and cost.

SUMMARY OF THE INVENTION

The present invention addresses challenges presented in the fabrication, alignment, and mounting of such monochromating optics in x-ray analysis systems. In that regard, the present invention, in one aspect, is a support structure having multiple highly aligned curved x-ray optics, the support structure having multiple internal partially or fully concentric surfaces upon which said optics are mounted, thereby aligning said optics along a central optical axis thereof and therefore to a source, sample, and/or detector in combination with which the support structure is useable.

The surfaces may be nested around the central optical axis; and the support structure may be divided longitudinally into sections around the central optical axis by walls.

At least one of the x-ray optics comprises a curved diffracting optic, for receiving a diverging x-ray beam and focusing the beam to a focal area, in one embodiment a focusing monochromating optic.

In an improved embodiment, the optic comprises a single layer, plastically deformed, LiF optic.

The optic may comprise multiple segments, each segment bent into a curved shape, and arranged into a curved pattern within the support structure.

A first x-ray optic may monochromate first energy from a source of x-rays and a second optic may monochromate a second energy or bremsstrahlung energy from the source of x-rays.

In another embodiment, the present invention is directed to a curved, monochromating x-ray optic, and method of forming the same, comprising a single layer of material, plastically deformed into a shape for receiving and redirecting x-ray energy. The material may be LiF, and the optic may be singly or doubly curved.

The optic may be formed by heating a single layer of material and bending the layer while heated such that the layer retains its bent shape after cooling, with a structural rigidity allowing easy mounting in the support structure disclosed herein.

Further, additional features and advantages are realized by the techniques of the present invention. Other embodiments and aspects of the invention are considered a part of the claimed invention.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the accompanying drawings in which:

FIG. 8$b$ is a cross-sectional, elevational view of the optic of FIG. 8$a$, taken along line A-A;

FIG. 10$b$ is a perspective view of a single layer, 2-dimensionally curved optic, in accordance with the present invention;

FIGS. 13A-13C are exemplary graphical user interfaces of the analyzer of FIG. 11 and/or FIG. 12.

DETAILED DESCRIPTION OF THE INVENTION

As discussed above, monochromating and focusing optics can provide benefits in x-ray analyzers. Two "engine" approaches for such analyzers are discussed briefly: MWDXRF and ME-EDXRF.

Exemplary MWDXRF X-Ray Analysis Engines:

The assignee of the present invention has previously disclosed a Monochromatic Wavelength Dispersive X-ray Fluorescence (MWDXRF) analyzer using an engine having two monochromating optic sets (U.S. Pat. Nos. 6,934,359 and 7,072,439—hereby incorporated by reference herein in their entirety), as shown schematically in FIG. 1. A related SINDIE (Sulfur IN DIEsel) product line for the measurement of sulfur in diesel fuel and other fuel distillates revolutionized XRF and provides many advantages including: (1) signal/background (S/B) is improved due to monochromatic excitation of the sample by DCC1, i.e., the bremsstrahlung photons with energies under fluorescence peaks (which normally swamp these peaks of interest) can only reach the detector through scattering, therefore improving the S/B ratio dramatically compared to polychromatic excitation; (2) superior energy resolution—this eliminates all common interference problems and provides the physical basis for upstream applications; (3) inherent robustness and low maintenance—the analysis engine is low power, compact, with no moving parts or consumable gasses; and (4) unprecedented dynamic range, e.g., a quantification level from 0.3 ppm to 5% of sulfur in a sample.

Figure 1:
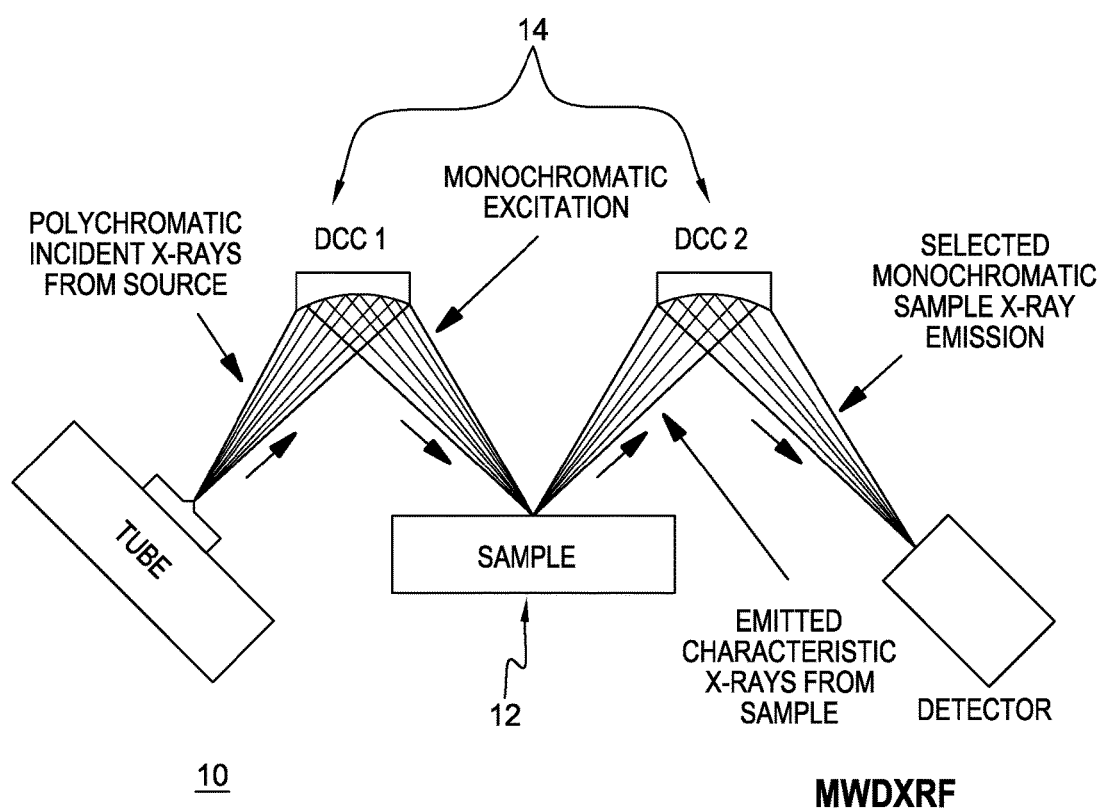
FIG. 1 is a schematic view of an exemplary MWD XRF x-ray engine useable with the support structure and optics of the present invention.

The MWD XRF engine 10, shown schematically in FIG. 1, includes curved monochromating optics 14 in the excitation and detection paths, forming a focal area on a sample 12, which is the configuration of the SINDIE sulfur analyzer discussed above. However, an optic may only be present in one of these paths, which still requires precise alignment. In one example, an optic of any of the herein-described types may only be present in the excitation path, and the detection path would include an energy dispersive detector. This is the common configuration of an energy dispersive x-ray fluorescence (EDXRF) system.

Figure 2:
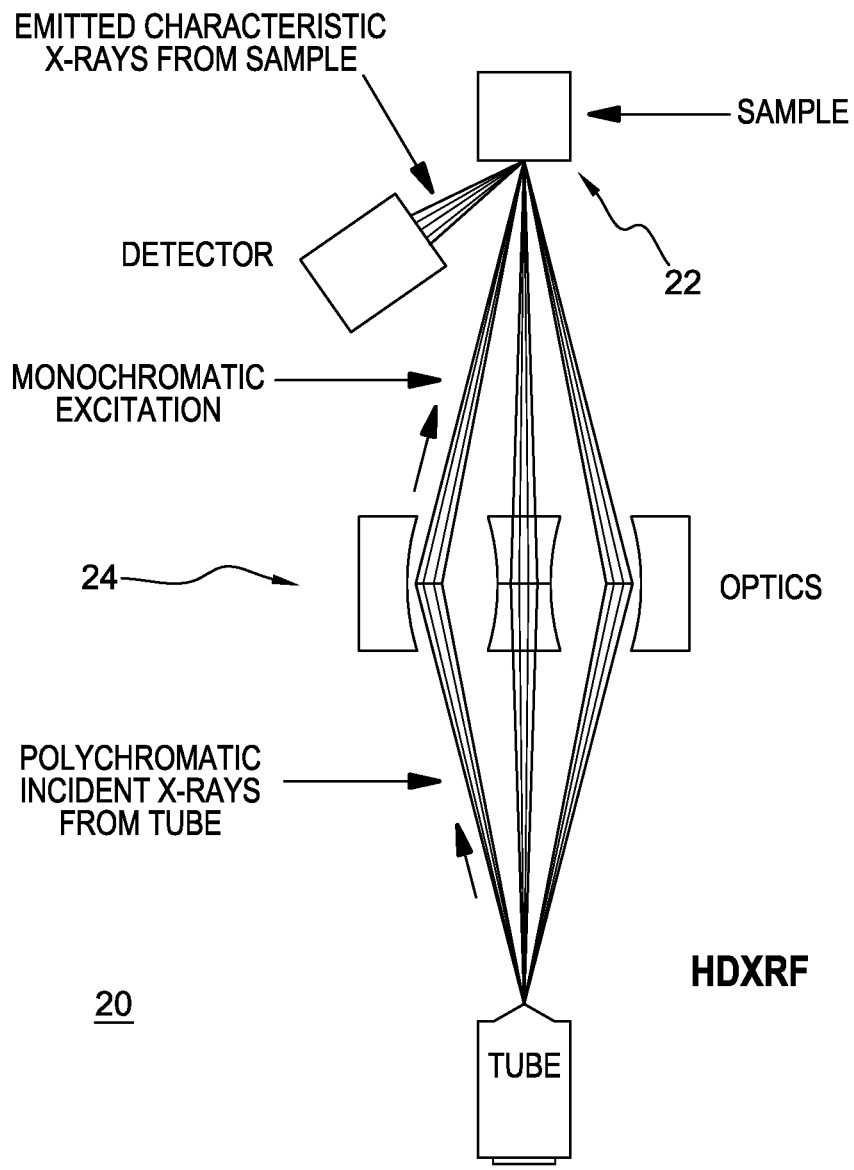
FIG. 2 is a schematic view of an exemplary ME EDXRF x-ray engine useable with the support structure and optics of the present invention.

Exemplary ME EDXRF X-Ray Analysis Engine:

Monochromatic excitation, energy dispersive x-ray fluorescence (ME-EDXRF) analyzers can also benefit from the herein-described optics technology. Such engine technology is disclosed in, e.g., commonly assigned US Publication 2011-0170666A1 and PCT Publication No. WO 2009111454 (A1) entitled XRF SYSTEM HAVING MULTIPLE EXCITATION ENERGY BANDS IN HIGHLY ALIGNED PACKAGE, the entireties of which are hereby incorporated by reference herein. In one embodiment this engine 20 involves monochromatic excitation known as HDXRF as depicted schematically in FIG. 2. HDXRF is a multi-element analysis technique offering significantly enhanced detection performance over traditional ED or WD XRF. This technique applies multiple, state-of-the-art monochromating and focusing optics 24 illuminating a focal area 22 on a sample, enabling multiple select-energy excitation beams that efficiently excite a broad range of target elements in the sample. Monochromatic excitation dramatically reduces scattering background under the fluorescence peaks, greatly enhancing elemental detection limits and precision. HDXRF is a direct measurement technique and does not require consumables or special sample preparation.

Figure 3:
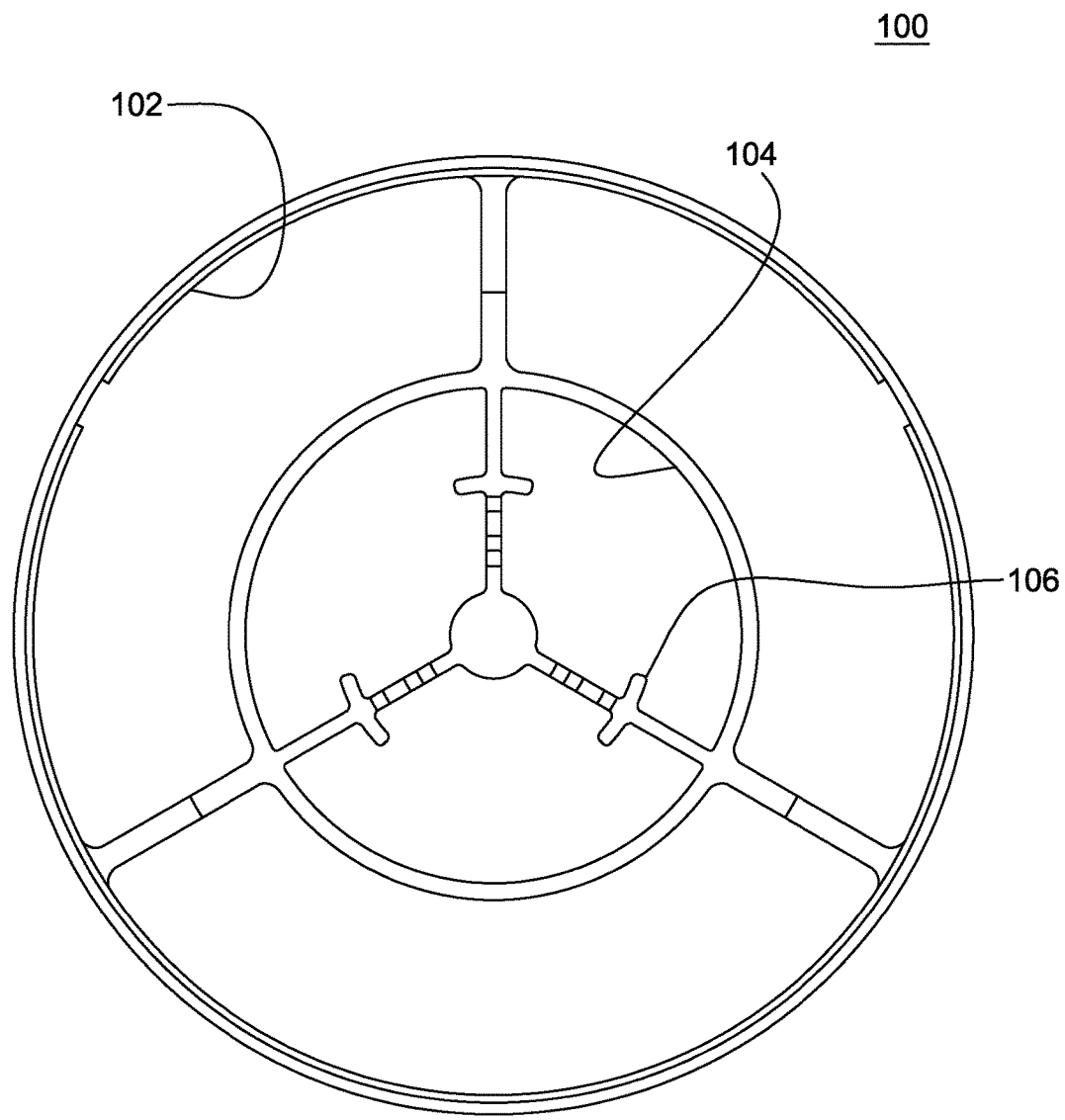
FIGS. 3-4 are an end view and perspective view, respectively, of an un-populated optic support structure, in accordance with an aspect of the present invention.
Figure 4:
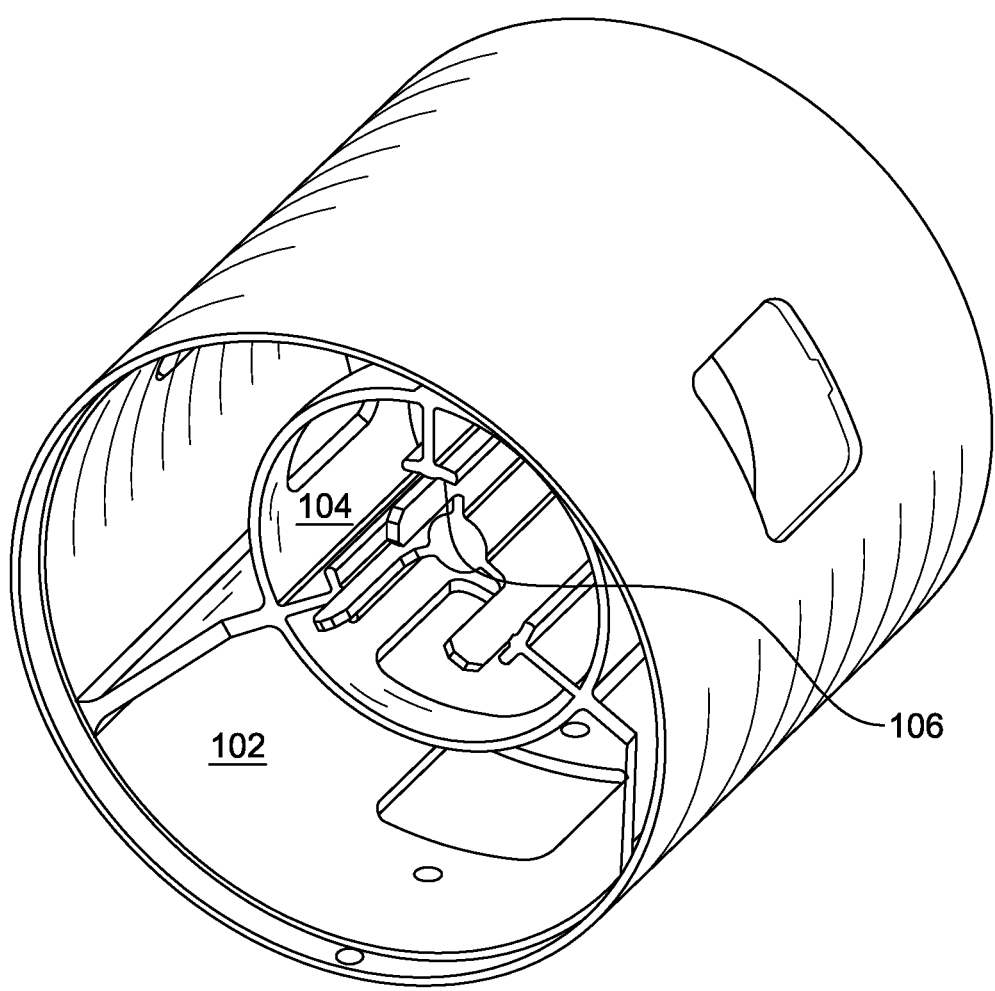

Exemplary Support Structure for Monochromating Optics:

Advanced x-ray analyzers such as those discussed above require improved mounting apparatus for multiple x-ray optics, and/or optics formed from multiple sections which together approximate a single optic. (The word optic is used broadly herein to connote a single segment, the majority or totality of which is used to focus and/or monochromate incident x-rays; or an individual segment of multiple segments, the entirety of which operate in combination to focus and/or monochromate incident x-rays.) With reference to FIGS. 3-4, shown therein is a support structure 100 for multiple, highly aligned optics in accordance with the present invention. The structure may have partially or fully concentric inner surfaces 102, 104 upon which optics are mountable; and/or other tab-like guides or structures 106 upon which optics are mountable. The surfaces may be nested around a central optical axis as shown. The structure can be used to mount x-ray optics including those disclosed herein and in the herein-incorporated documents, in accordance with the present invention. The structure may be cast into a unitary metal structure or formed from individual (e.g. metal) sheets.

Figure 5:
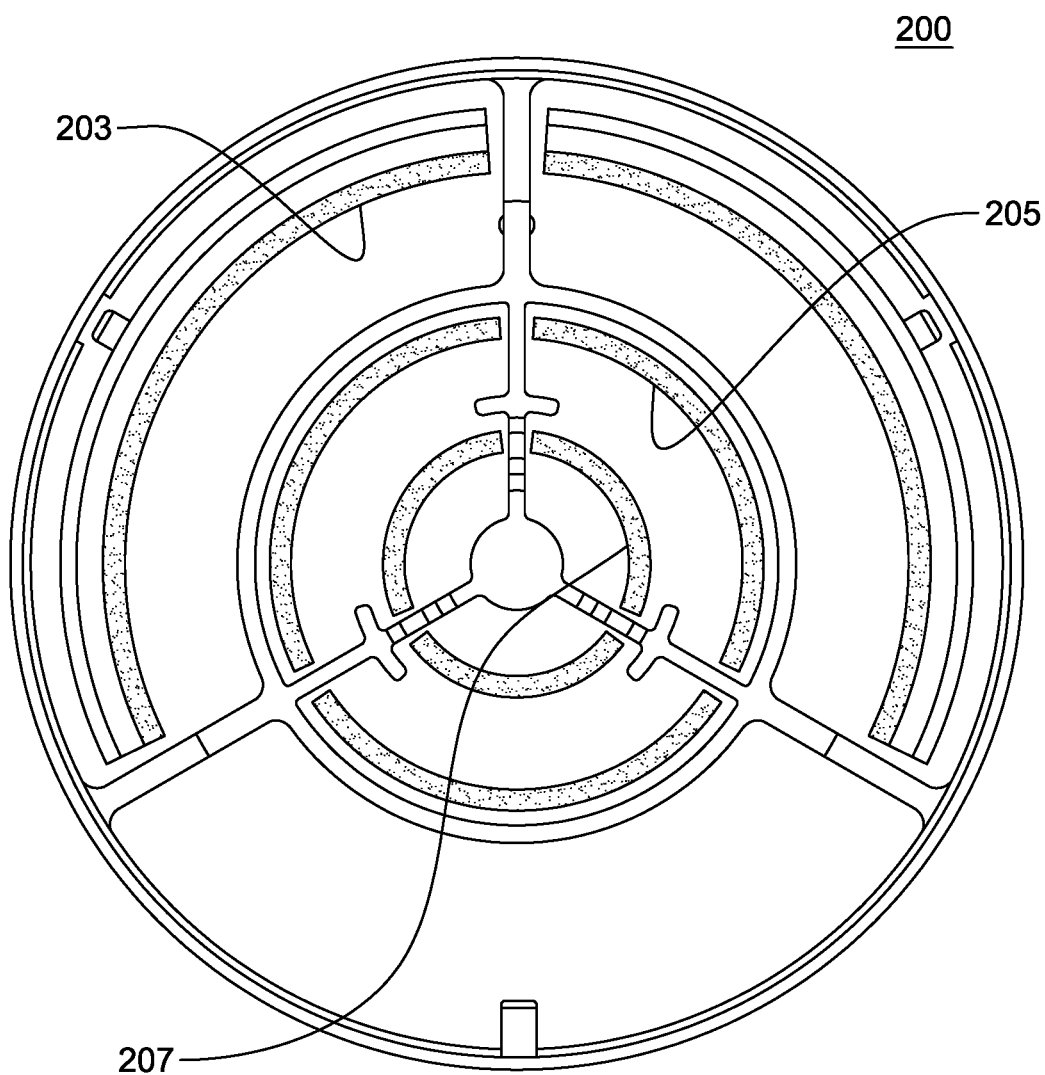
FIGS. 5-6 are an end view and perspective view, respectively, of an optic support structure populated with single-piece monochromating optics, in accordance with an aspect of the present invention.
Figure 6:
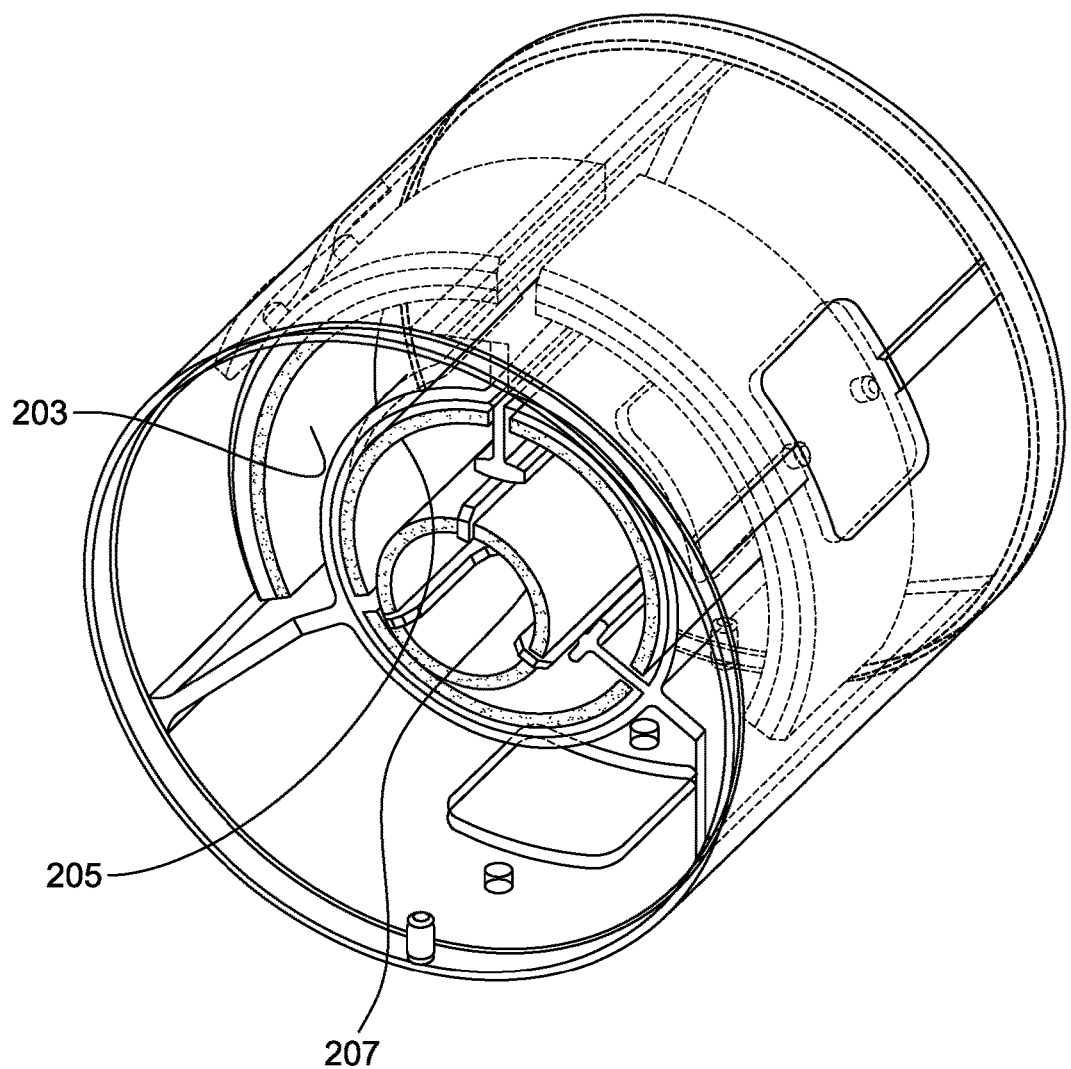

As shown in the fully populated structure 200 of FIGS. 5-6, partially or fully circular optics 203, 205, 207 are mounted therein, and, for example, aligned with their input and/or output focal points aligned along the central axis. Mounting can occur using glue or other bonding compounds, or other mechanical mounting features. In this example, "low energy" optics 203 may be formed from two segments over about a 240 degree rotation; and "medium energy" optics 205 and "high energy" optics 207 may be formed from 3 segments around a full 360 degree rotation as shown in the support structure. In this example embodiment, optic 203 is a layered optic, and optics 205 and 207 comprise single layer optics, as discussed further below.

Features and advantages of this support structure include:
The ability to align optics along the optical axis without necessitating insertion into the other active parts of an x-ray engine (i.e., tube and detector portions) during fabrication. With a precisely fabricated and aligned support structure, the optics are mounted in the structure and automatically aligned to its central axis (and to the tube, sample, and/or detector in e.g., FIGS. 1 and 2 above) and as the populated structure is inserted into the engine (at a later part of the production process) the optics are automatically aligned within the engine. This negates the need for a costly and time-consuming step of individual optic alignment within an engine, earlier in the production process.
Less parts—in a preferred embodiment using mounting compound, no separate mechanical mounting parts are required.
Circular X-ray apertures (not shown) which control the illumination path into and out of the support structure can be easily mounted onto the circular ends of the support structure.
Robustness in the form of strong cylindrical construction, and with three supporting internal walls forming the 120 degree internal sections, which has been shown to add extra strength. This is especially important for handheld analyzers (FIG. 12 below) which may be subject to dropping, etc.

Exemplary types of optics mountable in the support structure are briefly discussed below with respect to the populated structure of FIGS. 5-6. However, in general, x-ray optics may include, for example, curved crystal monochromating optics such as those disclosed in commonly assigned U.S. Pat. Nos. 6,285,506; 6,317,483; 7,035,374; and 7,738,629; and/or multilayer optics; and/or HOPG optics; and/or x-ray filters; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506 and 7,209,545 are also useable. Each of the above-noted patents and patent applications is hereby incorporated herein by reference in its entirety.

Low Energy DCC Optic—203:

Two different types of exemplary, low-energy DCC optics are disclosed herein as examples only—one with a 5.4 keV diffraction energy and 80 mm input focal distance (IFD); the other may have a 7 keV diffraction energy and 120 mm IFD. The shorter input focal distance is designed in the event that a more compact system is desired. Two exemplary crystal materials are disclosed: germanium (Ge) (111) and pentaerythritol (PET)(002).

Medium Energy DCC Optic—205:

Two types of medium energy optics are disclosed using different crystal materials: silicon (Si) and lithium-fluoride (LiF). The targeted energy selected by the optic needs to be the strong characteristic line from the anode target material in order to maximize the performance of the optic. Other materials may be used for the efficient integration with a medium-energy source such as Mo $K_\alpha$ at 17.5 keV.

LiF(200) can increase the monochromatic beam flux for a curved crystal optic. LiF has a wide rocking curve and can capture more photons from a larger source spot size, therefore, the diffraction efficiency from a larger source spot size is higher than that of an Si crystal. Thus, the diffraction flux is much larger than the Si crystal for a larger source spot size (e.g., >500 μm). In addition, LiF may bend more readily than Si for the same thickness. Both optics made of Si and LiF may have a Johann geometry design, as discussed elsewhere herein.

High Energy DCC Optic—207:

The medium-energy optic is used to capture the characteristic line from the x-ray source, the most intense part of the polychromatic spectrum, while the high-energy optic may be used to capture the background, or Bremsstrahlung radiation from an exemplary Mo source. The Bremsstrahlung intensity is much lower than that of a characteristic line. Two exemplary high-energy optic-realization techniques are disclosed herein. The first aspect involves a layered doubly curved crystal (LDCC) optic design; and the second is the use of LiF for this optic in a single layer. The LDCC design is based on a multiple-layer technique to capture a broader bandwidth of the Bremsstrahlung energy in the 30-40 keV range. The LDCC optic may have a multiple-layer structure with each layer capturing an adjacent narrow bandwidth. LiF crystal material used in the medium-energy optic can also be used for this high-energy optic. The flux is increased with a same diffraction crystal area because LiF has a wider rocking curve, and a thicker LiF crystal has a higher diffraction efficiency. The flux can be greatly improved by increasing the diffraction area in the similar manner as discussed in the medium energy optic section and by collecting larger solid angles. If higher flux is required, the thickness of the LiF crystal can be increased because LiF is more readily bent. LiF can be used in thicker crystals than Si to increase the diffraction efficiency of the optic.

To achieve a high-intensity beam, geometries with very high collection solid angle are disclosed. A fully revolved ellipsoid point-to-point focusing of LiF is disclosed for this high-energy optic as shown in FIGS. 5-6. To achieve the full 360° ellipsoid optic, three similar ellipsoidal segments, each with about 120° rotational angles, are disclosed. The three segments are aligned to the same focal point and form a fully rotated optic. The total collection solid angle of this design can be >0.03 sr., which is about 40× larger than previous designs. Because the slight change of the incident angles for a point source emitting from the focus of the ellipse, the reflection energy bandwidth is broadened. The bandwidth is estimated to be about 10% of energy for a 30 keV optic with focal length of 80 mm, and optical length of 45 mm.

An alternative approach is also disclosed using an MgO crystal material for the high-energy optic. Using MgO (220) wafers, the angle between the plane (220) and the crystal surface can be controlled precisely. This will allow the use of a stepwise approximation of the Johansson geometry (discussed elsewhere herein). Another benefit of MgO (220) is that the Bragg angle is larger compared to LiF (200). The larger Bragg angle will enable increasing the collection solid angle of an optic. The drawback of using MgO crystal is that the integral reflectivity is lower compared to LiF.

The spot sizes attainable with any of the above-described focusing optics can range from approximately 0.4 mm to 0.8 mm to 1.0 mm to 2.0 mm in diameter, facilitating analysis of small features on consumer products. In addition, the optics may produce spot sizes in any shape, depending on the shape of the optic.

Optic Realization Techniques:

As a first example, any of the layered optics discussed above can be implemented according to the techniques described in the commonly assigned, previously-filed U.S. Patent Application entitled X-RAY FOCUSING OPTIC HAVING MULTIPLE LAYERS WITH RESPECTIVE CRYSTAL ORIENTATIONS, U.S. Pat. No. 7,738,629 issued Jun. 15, 2012, the entirety of which is hereby incorporated by reference herein.

Figure 7:
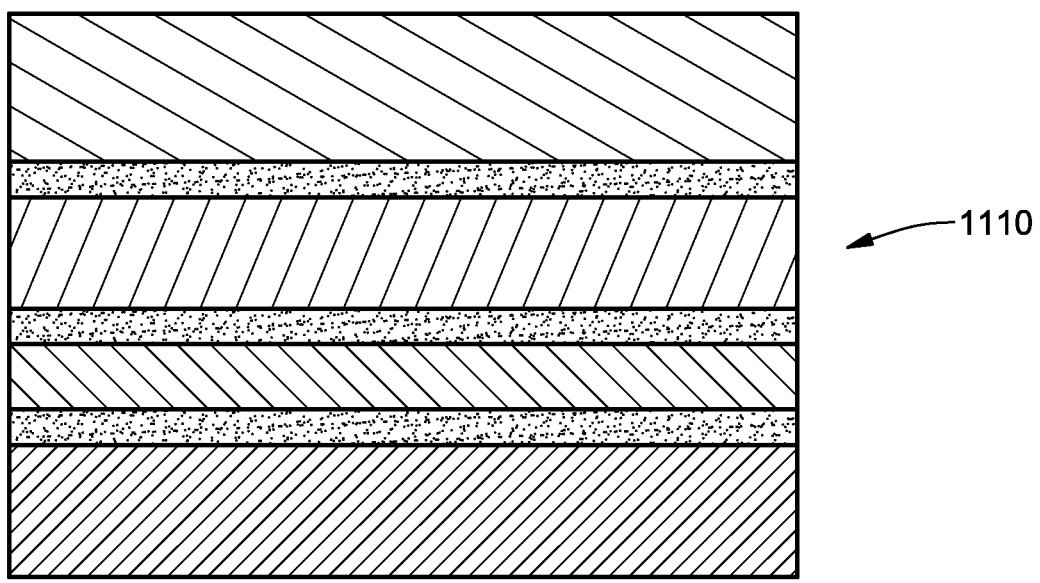
FIG. 7 depicts a finished, 4-layer monochromating optic, in accordance with an aspect of the present invention.

FIG. 7 shows a cross section of a portion of one such resulting thin, layered structure 1110 having four finished layers, each with its own, predetermined crystalline orientation. Though four layers are shown in this example, the present invention can encompass any plurality of layers, depending on design parameters. And, not all the orientations need to be different. By pre-determining the crystalline orientation of each layer, the diffraction properties of the structure as a whole can be optimized.

Each individual crystalline layer may provide an individual diffractive effect. These diffractive effects can be separately modeled, and their collective effect in the final optic can then be predicted and implemented according to final design criteria. This stands in contrast to known "multilayer" optics, having many layers of angstrom/nanometer thicknesses, each without an individual diffractive effect, but wherein the interactions between the layers result in an overall diffractive effect.

In another aspect of the present invention, layers of differing material composition can be employed in the same optic, with either the same or differing crystalline orientations between the layers (or mixes thereof); and layers of similar (or the same) material composition can be employed, again with either the same or differing crystalline orientations between the layers (or mixes thereof). In any of these aspects of the present invention, material-on-insulator may be used, or adhesive (e.g., epoxy) layers can be used to bind adjacent crystalline layers in accordance with the sequence of steps discussed in this incorporated Application.

Figure 8A:
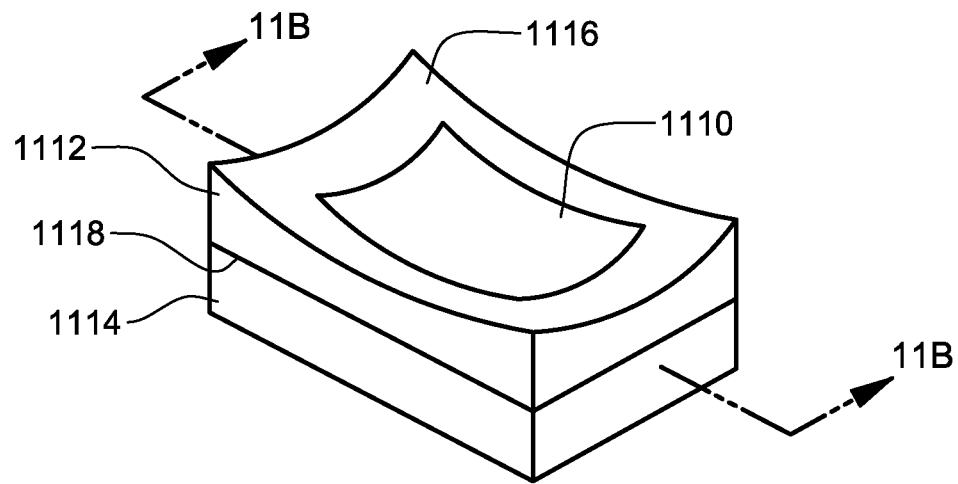
FIG. 8$a$ depicts another embodiment of a point-focusing, doubly curved monochromating optic.
Figure 8B:
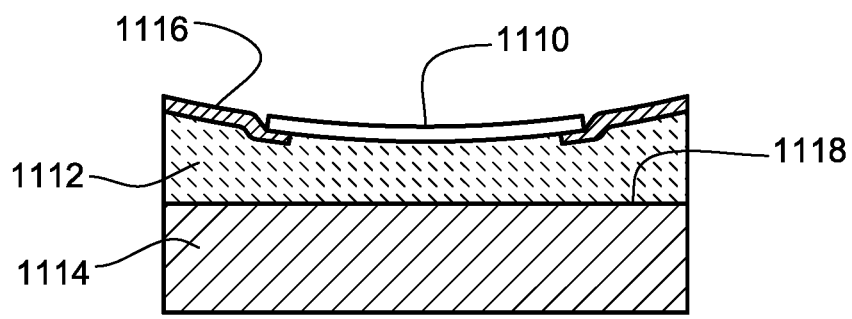

Structure 1110 can then be formed into a curved, monochromating optic, including a doubly-curved crystal (DCC) optic (or individual segments thereof). One embodiment of such a doubly-curved optical device is depicted in FIGS. 8a and 8b, and is described in detail in U.S. Pat. No. 6,285,506 B1, issued Sep. 4, 2001, the entirety of which is hereby incorporated herein by reference.

The layered optic structures offer the following advantages:
   The optic's mosaicity and rocking curves are controlled by layer orientation design.
   The efficiency of the optic is increased—each layer (with its own custom orientation) can have its own field of view, resulting in a composite field of view which increases efficiency and allows the optic to accommodate a larger source spot size. And, by accommodating a larger source spot size, system implementation is easier.
   The bandwidth (i.e., monochromatization) of the optic can be controlled, and, advantageously, increased in certain monochromating applications.

As another example, in the embodiment of FIG. 8a, a doubly-curved optical device can include the flexible layered optic 1110 (or a single layer optic), a thick epoxy layer 1112 and a backing plate 1114. The structure of the device is shown further in the cross-sectional elevational view in FIG. 8b. These configurations are disclosed in commonly assigned U.S. patent entitled CURVED OPTICAL DEVICE AND METHOD OF FABRICATION, U.S. Pat. No. 6,285,506 issued Sep. 4, 2001, the entirety of which is hereby incorporated herein by reference.

In this device, the epoxy layer 1112 holds and constrains the flexible layer 1110 to a selected geometry having a curvature. Preferably, the thickness of the epoxy layer is greater than 20 µm and the thickness of the flexible layer is greater than 5 µm. Further, the thickness of the epoxy layer is typically thicker than the thickness of the flexible layer. The flexible layer can be one of a large variety of materials, including those discussed herein. The epoxy layer 1112 can be a paste type with viscosity in the order of $10^3$ to $10^4$ poise and 30 to 60 minutes pot life. The backing plate 1114 can be a solid object that bonds well with the epoxy. The surface 1118 of the backing plate can be flat (FIG. 8a) or curved, and its exact shape and surface finish are not critical to the shape and surface finish of the flexible layer. In the device of FIGS. 8a-b, a specially prepared backing plate is not required.

Surrounding the flexible layer may be a thin sheet of protection material 1116, such as a thin plastic, which is used around the flexible layer edge (see FIG. 8a). The protection material protects the fabrication mold so that the mold is reusable, and would not be necessary for a mold that is the exact size or smaller than the flexible layer, or for a sacrificial mold.

Figure 9:
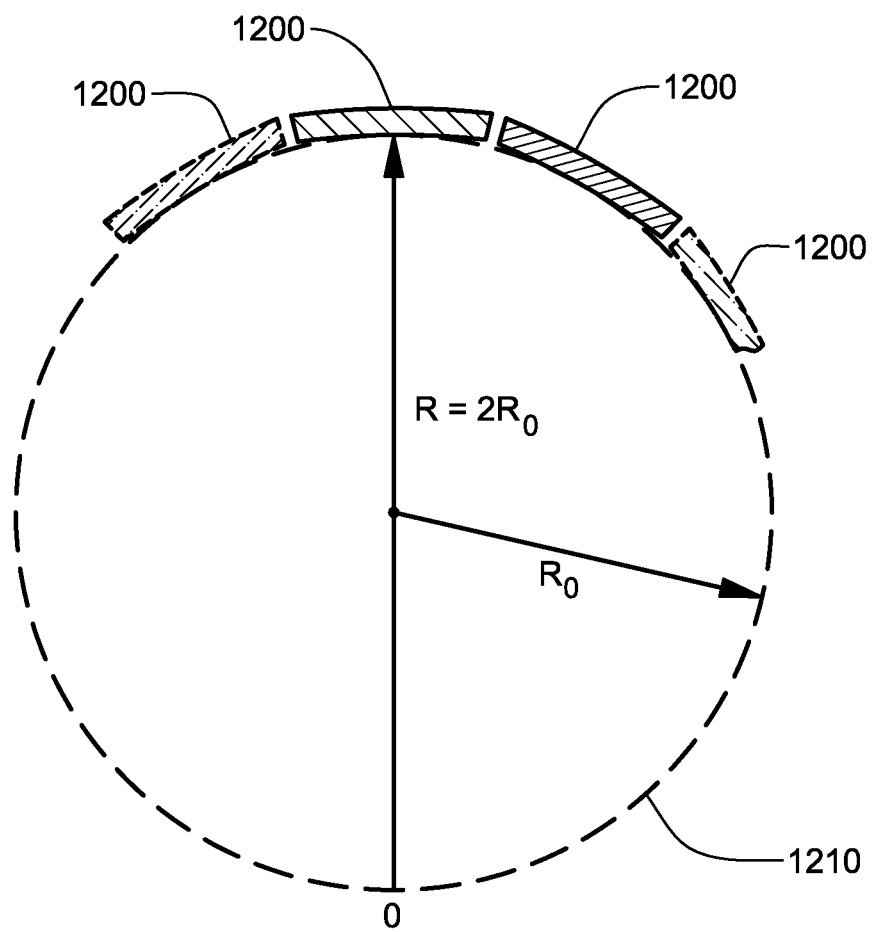
FIG. 9 depicts another possible embodiment of a focusing, curved monochromating optic (and illustrating Rowland circle geometry) using multiple instances (similar or different) of the above-described optic structures.

Any of the optics disclosed herein can be shaped in any way depending on the application, including but not limited to single directions of curvature (singly curved crystals—SCCs), double directions of curvature (doubly curved crystals—DCCs), and other designs. Doubly-curved optical devices, such as doubly-curved crystal (DCC) optics, may be used in material analysis to collect and focus x-rays from a large solid angle and increase the usable flux from an x-ray source. Three-dimensional focusing of characteristic x-rays can be achieved by diffraction from a toroidal crystal used with a small x-ray source. This point-to-point Johan geometry is illustrated in FIG. 9. The diffracting planes of each crystal optic element 1200 can be parallel to the crystal surface. If the focal circle 1210 containing a point source and the focal point has radius $R_0$, then the crystal surface has, for example, a radius R of curvature of $2R_0$ in the plane of the focal circle and a radius of curvature of $r=2R_0 \sin^2\theta_{Brag}$ in the perpendicular plane, with the radius centered on a line segment drawn between the source and the focal point. X-rays diverging from the source, and incident on the crystal surface at angles within the rocking curve of the crystal will be reflected efficiently to the focal or image point. The monochromatic flux density at the focal point for a DCC-based system is several orders of magnitude greater than that of conventional systems with higher power sources and similar source to object distances. This increase yields a very high sensitivity for use in many different applications, including (as described herein) x-ray fluorescence and diffraction.

As a further enhancement, FIG. 9 illustrates that the optical device may comprise multiple doubly-curved crystal optic segments 1200 arranged in a grid pattern about the Rowland circle, each element formed from a flexible structure 1110 as discussed above (either with similar or different element-to-element layer structures). Such a structure may be arranged to optimize the capture and redirection of divergent radiation via Bragg diffraction. In one aspect, a plurality of optic crystals having varying atomic diffraction plane orientations can be used to capture and focus divergent x-rays towards a focal point. In another aspect, a two or three dimensional matrix of crystals can be positioned relative to an x-ray source to capture and focus divergent x-rays in three dimensions. Further details of such a structure are presented in the U.S. patent entitled AN OPTICAL DEVICE FOR DIRECTING X-RAYS HAVING A PLURALITY OF OPTICAL CRYSTALS, U.S. Pat. No. 7,035,374 issued Apr. 25, 2006, the entirety of which is hereby incorporated herein by reference.

Figure 10A:
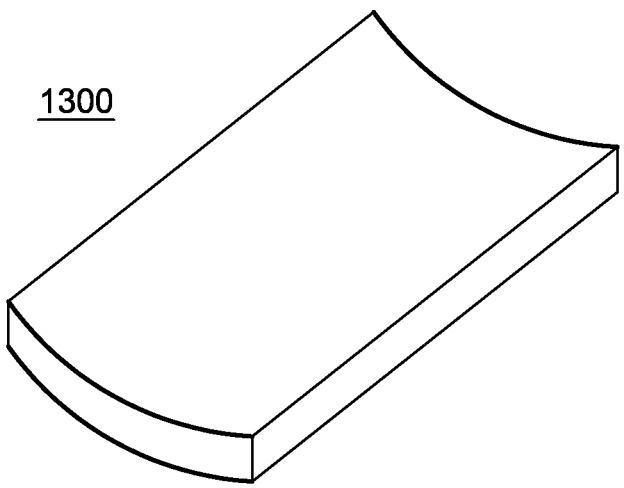
FIG. 10$a$ is a perspective view of a single layer, 1-dimensionally curved optic, in accordance with the present invention.
Figure 10B:
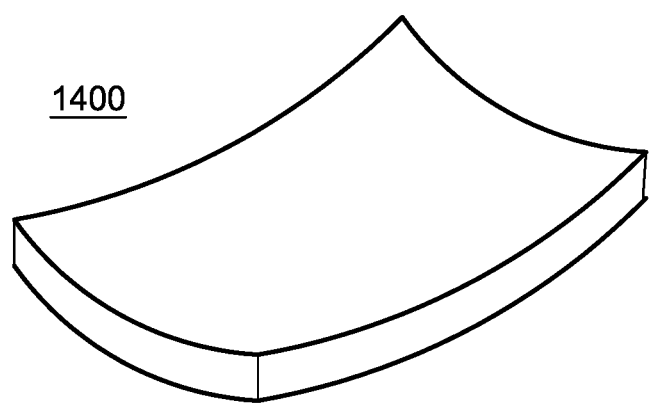

Single Layer Optics:

In another improvement, and with reference to FIGS. 10a-b, three-dimensional "single layer" optics 1300 and 1400 are depicted in accordance with the present invention. As mentioned above, for higher-energy applications, LiF may be a preferred selection for the optic material. High-energy photons can penetrate further into LiF; therefore, a thicker LiF DCC can provide higher efficiency. Thicker pieces of a single layer of LiF are therefore preferred for this purpose, as well as for the structural integrity needed to maintain a curvature, and for ease of placement into the support structure disclosed above.

Bending thicker LiF wafers into three dimensional shapes is the basis of making these high energy x-ray optics in accordance with the present invention. Because three-dimensional bending is proposed, stresses may be generated, and if this stress is beyond the fracture stress at <100>, it may crack the crystal. Although there is some plastic deformability of LiF at room temperature, it is typically not enough to tolerate and maintain three dimensional bending into functional optics.

The present inventors have discovered, that at elevated temperatures, LiF has increased capability to deform plastically and thereafter maintain its shape upon cooling, without any additional support. In accordance with the present invention, generally planar wafer sections are bent at elevated temperatures, and still maintain the precision shapes needed after cooling at room temperature, separate from their shaped tooling (not shown) or any other supporting layers or material.

For example, temperature in a heating chamber is increased toward 1000 degrees Celsius, or even higher. Shaped optic tooling with a desired curvature matching the desired optic curvature profiles shown in e.g., FIGS. 10a-b can be used to hold the LiF crystal in place in the heated chamber, and form it into a complementary shape to the tooling. The wafer then assumes the shape at a high temperature, and holds that shape as it is separated from the tooling, or any other supporting layers or material, and cools outside of the chamber.

Singly or doubly curved optics with a high energy of 98 keV and or even higher energy of 120 keV can be produced in this fashion. LiF wafer having a thickness of, e.g., about 0.5 mm can be used and provides the structural integrity required, as discussed above. Such optics can be used as, for example, the medium energy (205) and high energy (207) optics in the populated structure 200 shown in FIG. 6.

Figure 11:
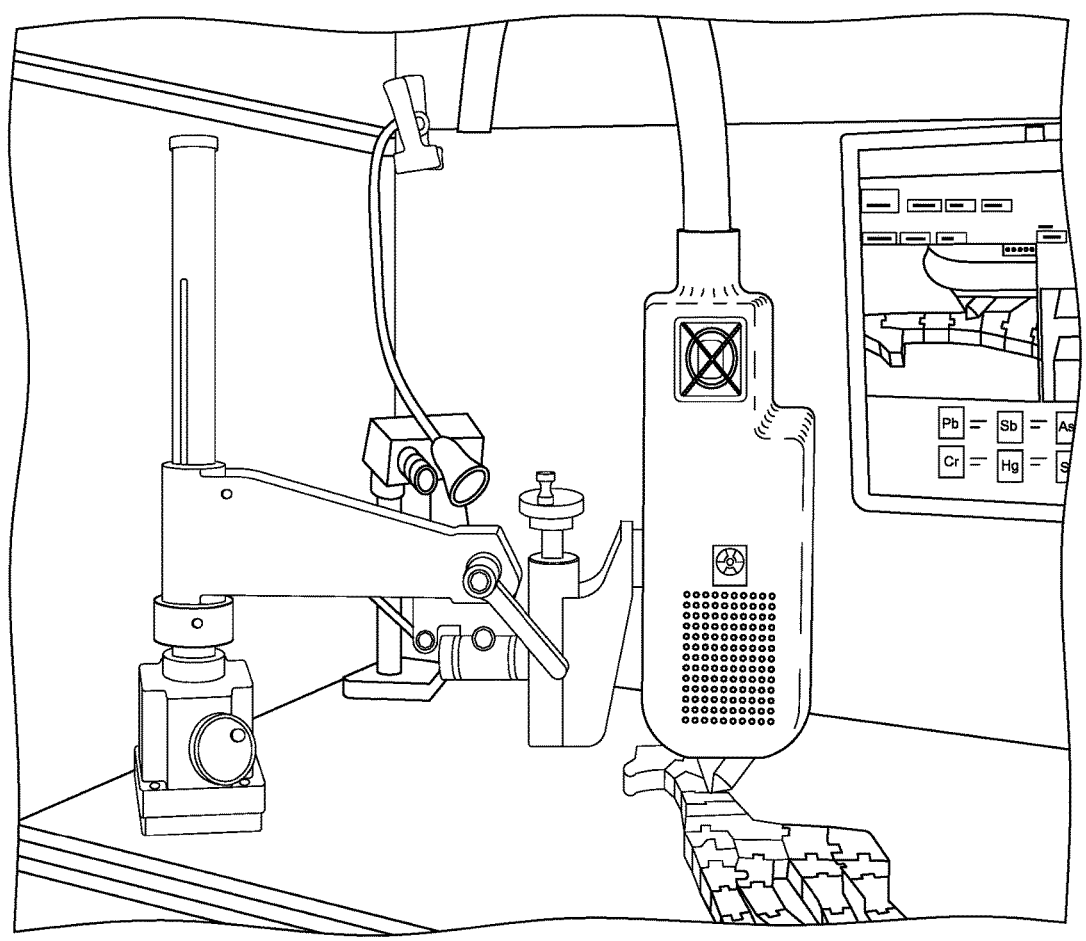
FIG. 11 is a perspective view of an analyzer having an x-ray engine suspended over a sample, in accordance with an aspect of the present invention.

Improved Analyzer System:

An exemplary ME EDXRF analyzer constructed in accordance with the present invention, using an exemplary SDD detector, an improved source, and low, medium, and high energy optics, is shown in FIG. 11, measuring a sample toy.

A fundamental parameter (FP) technique for monochromatic systems with Compton/Rayleigh (C/R) modeling may be used to process the x-ray fluorescence data detected from a sample stimulated with multiple, monochromatic beams generated by the optics and/or tubes discussed above. The FP technique is based on a single energy excitation beam and is suitable for bulk and homogenous measurements. Multiple monochromatic beams can be used, to sense different parts of the spectrum, and to de-convolute the toxins the painted layers and separately in the substrate.

A spectral processor (SP) may be used for fitting an energy dispersive X-ray fluorescence (EDXRF) spectrum based on multiple monochromatic beam excitation. The raw spectral data from the detector in a count vs. energy spectrum can be used for the input. A number of techniques can be utilized to account for various components in the spectrum such as a Gaussian modeling for peak fitting. Noise from the system and detector is also considered.

The fundamental parameters (FP) based technique is also useful for coating layer quantitative analysis. In this technique, the absorption, fluorescence, and scattering, are modeled based on a number of measured factors. Due to the use of monochromatic beams, the calculations can simplified, compared to the FP methods used for polychromatic excitation.

The layered-mode FP may require spectra from the combination of paint with the substrate, then from the substrate only, to resolve the separate compositions of a paint/substrate sample. One technical challenge is that the mass per unit area of the paint is unknown due to the low-Z elements (C, H, O) in the paint that cannot be detected. This mass per unit area for the coating, called $\rho t$ (density×thickness), should be determined in order to calculate the mass fraction of toxins. With two or more monochromatic beams, the toxin concentrations in the paint, and substrate separately, sample can be determined.

Figure 12:
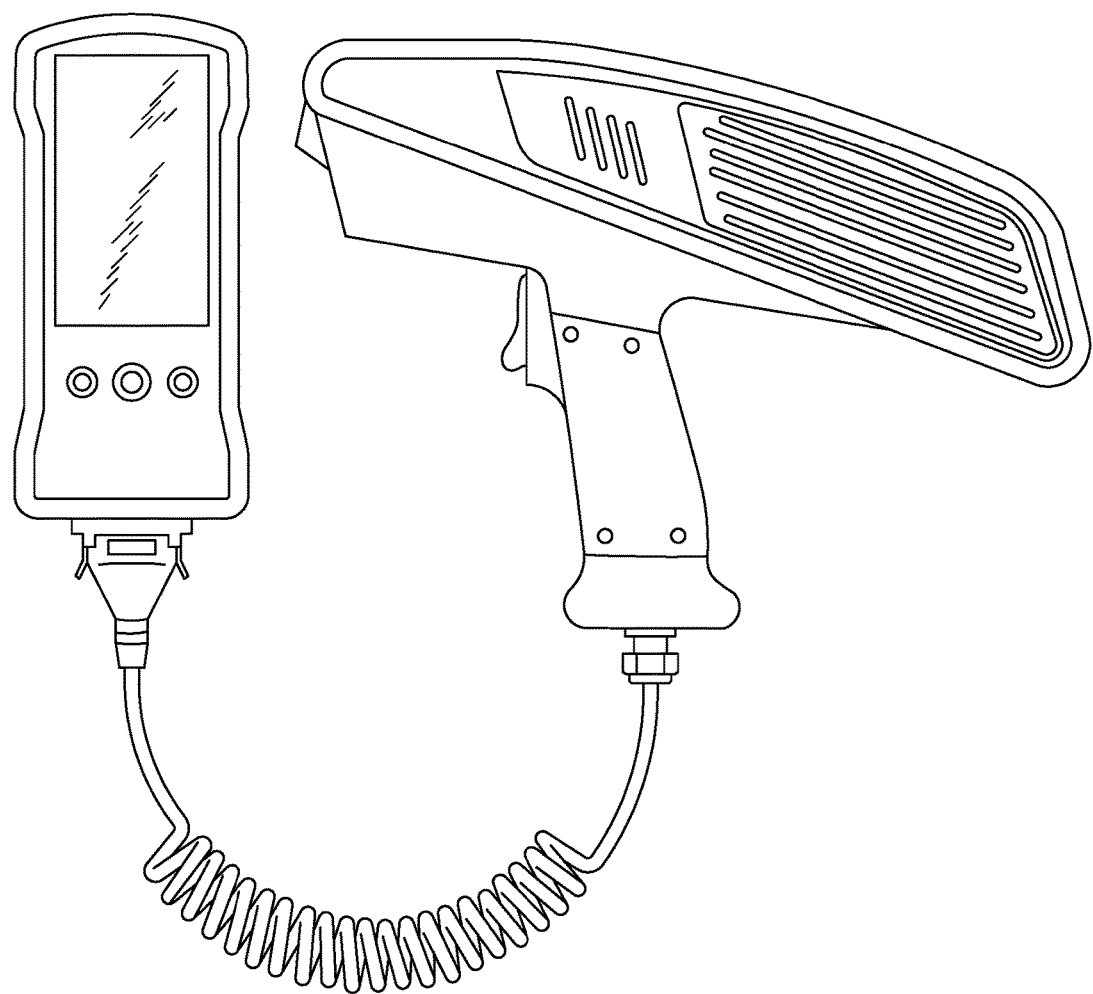
FIG. 12 is a perspective view of an exemplary handheld x-ray analysis instrument and related human interface module, in accordance with an aspect of the present invention.

Also, in accordance with the present invention, and with reference to FIG. 12, a smaller, "handheld" x-ray analyzer can also be implemented according to the principles of the present invention. Handheld x-ray analyzers have gained in popularity over the last few years because of their transportability and ease of use. Also shown in FIG. 12 is a human interface module, which may include the user interface, FP processor, and/or a power source for the handheld analyzer. Such an interface may also be integral to the analyzer.

Figure 13A:
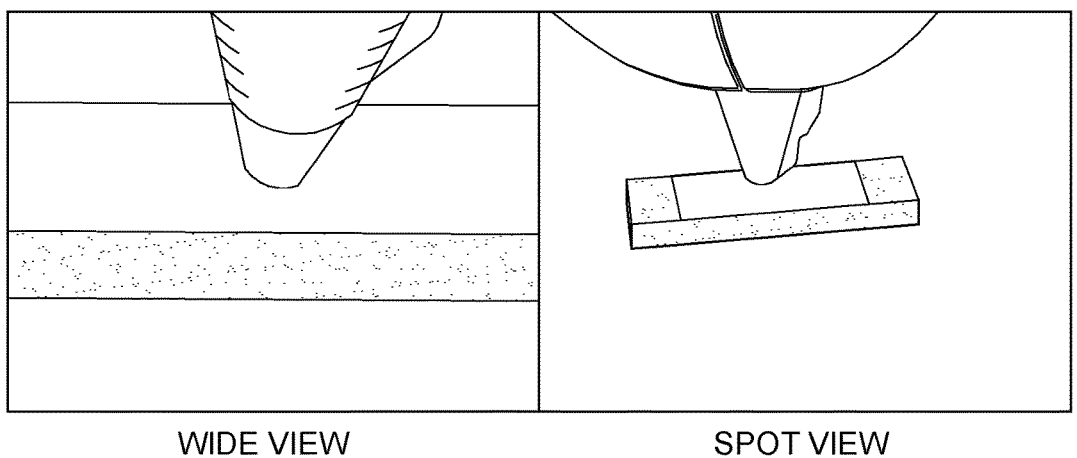
Figure 13C:
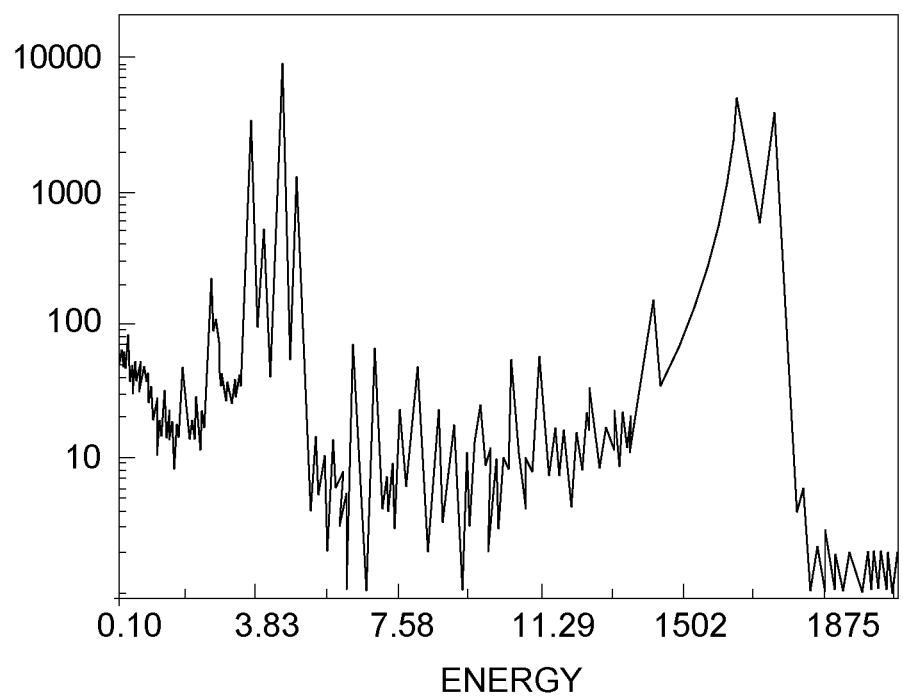

Example graphic user interfaces (GUIs) for either of these systems are shown in FIGS. 13A-13C. As shown, the exemplary GUI may allow user selection of sample types, display 10 element concentrations, and related spectra. The GUI may also display a live image of the sample to assist with sample positioning. Snapshots of the possible GUIs are shown in FIGS. 13A-13C.

Although preferred embodiments have been depicted and described herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A method of forming an x-ray analyzer, comprising:
   providing an x-ray excitation path for directing x-rays from an x-ray source toward a sample,
   providing an x-ray detection path for collecting fluorescence from the sample,
   wherein the excitation path includes at least two monochromating x-ray optics, wherein a first x-ray optic monochromates first energy from the x-ray source and a second optic monochromates bremsstrahlung energy from the x-ray source, and
   forming the at least two monochromating x-ray optics, including heating a single layer of LiF material and bending the layer while heated using shaped optic tooling with a desired curvature matching a desired optic curvature, such that the layer retains its bent shape after cooling.

2. The method of claim 1, wherein at least one of the at least two monochromating x-ray optics is single curved.

3. The method of claim 1, wherein at least one of the at least two monochromating x-ray optics is doubly curved.

4. The method of claim 1, wherein the detection path includes at least one further monochromating x-ray optic.

5. The method of claim 1, wherein at least one of the at least two monochromating x-ray optics is a focusing monochromating optic.

6. The method of claim 1, wherein at least one of the at least two monochromating x-ray optics is a doubly-curved crystal optic, or HOPG optic, or multi-layer optic.

7. The method of claim 1, wherein at least one of the at least two monochromating x-ray optics comprises a single layer, plastically deformed, LiF optic.

* * * * *